United States Patent [19]

Schulte et al.

[11] Patent Number: 5,199,873

[45] Date of Patent: Apr. 6, 1993

[54] DENTAL IMPLANT

[75] Inventors: Willi Schulte, Tübingen; Freimut Vizethum, Schwetzingen; Walter Hund, Oberkirch-Stadelhofen, all of Fed. Rep. of Germany

[73] Assignee: Friedrichsfeld AG Keramik- und Kunststoffwerke, Mannheim, Fed. Rep. of Germany

[21] Appl. No.: 642,344

[22] Filed: Jan. 15, 1991

[30] Foreign Application Priority Data

Jan. 15, 1990 [DE] Fed. Rep. of Germany ....... 4000914

[51] Int. Cl.$^5$ .............................................. A61C 8/00
[52] U.S. Cl. .................................... 433/174; 433/173
[58] Field of Search ........................ 433/172, 173, 174

[56] References Cited

U.S. PATENT DOCUMENTS

| | | | |
|---|---|---|---|
| 4,185,383 | 1/1980 | Heinke et al. | 433/173 |
| 4,552,532 | 11/1985 | Mozsary | 433/173 |
| 4,560,353 | 12/1985 | Schulte et al. | 433/173 |
| 4,609,354 | 9/1986 | Koch | 433/173 |
| 4,856,994 | 8/1987 | Lazzara et al. | 433/173 |
| 4,863,383 | 9/1989 | Grafelmann | 433/174 |
| 4,927,363 | 5/1990 | Schneider | 433/173 |

FOREIGN PATENT DOCUMENTS

| | | |
|---|---|---|
| 125203 | 11/1984 | European Pat. Off. |
| 2308962 | 9/1973 | Fed. Rep. of Germany |
| 2628443 | 12/1976 | Fed. Rep. of Germany |
| 3533395 | 5/1986 | Fed. Rep. of Germany |
| 2176709 | 1/1987 | United Kingdom ................ 433/174 |

*Primary Examiner*—John J. Wilson
*Assistant Examiner*—Cindy A. Cherichetti
*Attorney, Agent, or Firm*—Foley & Lardner

[57] ABSTRACT

A dental implant including a post which can be anchored in the jawbone of a dental patient and a replacement tooth head fastenable to said post. The post has at its crown end a recess for mounting a replacement tooth. The outside surface of the post is stepped down in at least two, and preferably three or four, steps to an apical root end opposite said crown end. At least one of the steps carries an external screw thread, and of two adjacent steps, the step closer to the apical root end has a thread crest diameter which is not larger than the base diameter of the adjacent step situated closer to the crown end of the implant.

20 Claims, 3 Drawing Sheets

DENTAL IMPLANT

The present invention relates to a dental implant comprising a post which is anchorable in the jaw and which has a recess at the crown end for fastening a head of a replacement tooth, wherein the outer surface of the post is configured to form an apical or root end having at least two steps.

A dental implant of this kind, whose crown end has a provision for anchoring a superstructure, is disclosed in U.S. Pat. No. 4,185,383. The dental implant contains a post or stem which can be implanted in the jawbone, and is repeatedly stepped downward from the head toward the root. The surfaces of the steps facing the root end are perpendicular to the long axis of the post. The dental implant has a tissue-compatible surface of high-purity, nonporous aluminum oxide ceramic, a portion of smaller cross section being provided in the area of the gingival line and configured as a circumferential constriction of the head. This dental implant has proven good in practice in the past, and is known in the art as the "Tubingen implant". The head and the post form an integral unit. After implantation, before the superstructure is attached, while the post is establishing itself in the jawbone, unacceptable forces may be exerted on the head portion in the area of the gingival line, which can adversely affect the adaptation of the tissue to the post and the formation of bone as well as the anchoring of the post.

U.S. Pat. No. 4,863,383 discloses a screw-type dental implant whose post has a self-tapping thread on its outer surface. For this purpose a pilot hole which has a uniform diameter over its entire length is drilled in the jawbone. The post has a core which tapers toward the root end and is provided externally with the self-tapping thread. The thread depth decreases steadily to zero from the root end toward the crown end and the head portion situated at the crown, the outside diameter of the thread being made constant over the entire length. The thread must be screwed the entire length of the post into the prepared bore in the jawbone, while being careful not to traumatize the cortex. Screwing the thread the entire length of the post requires a correspondingly long time of operation, inasmuch as screwing it in too fast increases the danger of traumatizing the cortex. Furthermore, difficulties can arise if the axis of the post initially is not in alignment with the axis of the bore in the jawbone, resulting in unacceptable damage to the bore wall by the skewed introduction of the root end of the post.

A dental implant is disclosed in U.S. Pat. No. 4,560,353 having a plate-like post containing steps with openings, in which the step surfaces are disposed so as to face toward the jawbone, and a cylindrical portion is provided in the area where it emerges from the gum. The cylindrical portion bears a ring of bioinert ceramic with an annular groove in the outside. This cylindrical, post-like portion contains a blind hole for mounting the head part of a superstructure or substitute tooth. Before the plate-like part can be inserted into the jawbone, the jawbone must be drilled out to conform to the elongated, stepped configuration, and this calls for considerable operating time. Furthermore, an ideal match to the geometry of the post can hardly be achieved in practice, so that the primary stability often fails to satisfy requirements after the implantation.

Also, U.S. Pat. No. 4,609,354 discloses a bone implant composed of two parts which can be joined together. The one post part that can be placed in the jawbone has a bore into which a stud of the other, head part serving for the mounting of the replacement tooth can be replaceably inserted. The stud is held in the bore of the post part by a friction fit. The diameter of the stud and the bore are adapted to one another such that, at body temperature, the stud seizes in the bore and can be extracted from the bore when the temperature is lowered. Difficulties can arise with such two-part constructions, especially if there is a gap between the two parts in which bacteria can settle. On the other hand, however, the advantage is achieved that, first the post part is implanted, and after the gum closes over it, bone growth and fixation can take place undisturbed by external influences. Not until the healing process is at least largely completed is the head part inserted after reopening of the gum, and finally the superstructure or replacement tooth is anchored in the necessary manner.

SUMMARY OF THE INVENTION

It is the object of the invention to provide a dental implant which makes it possible to anchor a replacement tooth in a functionally secure manner using an operating technique which decreases the risk of trauma.

It is also an object of the invention to provide a dental implant which is constructed so that it can be implanted in a short time.

Another object is to provide a dental implant which functions reliably to assure convenient handling during and after implantation.

A further object of the invention is to provide a dental implant which can grow into the jawbone without being disturbed by external influences.

Yet another object of the invention is to provide a dental implant reduces the occurrence of undesirable gaps and/or transitions which adversely affect the formation of the gum after the substitute tooth is installed.

A still further object is to provide a dental implant which reliably meets requirements for high resistance to bacterial penetration.

These and other objects of the invention are achieved by providing a dental implant comprising a post anchorable in a jawbone of a dental patient and a replacement tooth head fastenable to said post, the post having a crown end provided with means for attaching said replacement tooth head and the post further having an outer surface configured to form an apical root end opposite the crown end, the outer surface having at least two steps with each step toward the apical root end having a respective base diameter which is smaller than the base diameter of the adjacent step toward the crown end, at least one of the steps carrying a screw thread; wherein each step which carries a thread has a thread crest diameter which is at most equal to the base diameter of the adjacent step situated toward the crown end, and wherein upon implantation the post can be freely inserted into a stepped bore in the jawbone down to all but one last step length and then can be screwed this last step length further into the jawbone.

The dental implant of the invention assures a functionally reliable anchoring of the substitute tooth. At least one stepped portion of the post has a screw thread, and during implantation the post part can be inserted into the jawbone leaving only one step exposed, and then the post only needs to be screwed into the jawbone to a depth corresponding to the length of that one step.

In contrast to previously known implants which are screwed in over the entire length of the thread, a comparatively nontraumatic operating technique is thereby provided, since the screwing has to be done over only a fraction of the total length of the thread or post. For example, if four steps are provided, the post is simply inserted into the bore in the bone to ¾ of its total length and then is screwed in by only ¼ of its length, thereby very elegantly avoiding any traumatizing of the cortex by the screw thread. The screw thread provided on at least one step results in better primary stability in comparison with posts that have no thread and whose entire length is inserted into the bore in the bone. The proposed special configuration also assures quick implantation, inasmuch as the simple insertion of the post already achieves a good alignment of the post with the longitudinal axis of the bore, and when the screwing begins the axis of the post is in line with the longitudinal axis. The step at the crown end advantageously may have a cylindrical outer surface to assure intimate contact with the inside wall of the portion of the bore that has the largest diameter. In a particularly preferred embodiment, there are no threads or mechanical retaining means in the area of the uppermost step with the greatest diameter, which significantly improves hygiene in the area of an implant.

At least two, preferably three, steps are threaded, each having the same length. This substantially improves implantation and screwing in of the post because, before any rotational motion and cutting of threads occurs, the post can be inserted into the jawbone, which is bored with matching steps, until virtually all that is lacking is the length of only one more step to reach the final depth of implantation. Then the post needs only to be turned with the self-tapping threads for the length of just one step and anchored in the jawbone. The result is a substantial reduction in the stress and strain on the tissues in comparison with a thread having a substantially uniform diameter over its entire length. Particularly if three steps are provided, and the threads can be given, for example, four turns on the longitudinal axis to cover the length of the step, then four turns are all that are needed to anchor the post fully. In comparison, a post without steps and with a diameter that is constant over three times the length of one such step, and threaded with the same pitch as in the stepped configuration according to the invention, would require a total of twelve turns to be anchored. Even so, the dental implant of the invention is supported by the entire length of the threads on the steps. Due to the stepped configuration of the post and the fact that the outside diameter of the threads of the step next to the root end is made equal to or less than the outside diameter of the preceding step, the tissues are optimally protected in an especially reliable manner.

In one preferred embodiment, the bottom face of the head lies tightly against the post anchored in the bone, thus reliably preventing the entry of bacteria. The bottom face of the head is axially biased against the upper face of the post. The head is a component that is premanufactured and packaged and consists especially of metal. The post is advantageously coated with hydroxyapatite, while the head is provided with a ceramic coating, particularly in the area of the face and adjacent surfaces. The face of the head is a planar surface orthogonal to the longitudinal axis. The ceramic coating, which of course is extremely hard, can be worked and ground flat as necessary with comparatively little difficulty. The head advantageously may comprise two parts, namely the actual crown holder and a coupling means which is to be fastened in a bore in the post. The crown holder includes the aforementioned ceramic-coated face which provides the tight, gap-free contact under bias, with the corresponding face of the post. Since the head is joined directly to the post, no spacing sleeve is needed. The crown holder or head and the post contact each other at a single area, namely between the aforementioned face and the bearing face of the post.

BRIEF DESCRIPTION OF THE DRAWINGS

The invention will be explained in further detail with reference to an illustrative preferred embodiment shown in the accompanying drawings wherein.

DETAILED DESCRIPTION OF PREFERRED EMBODIMENTS

Figure 1:
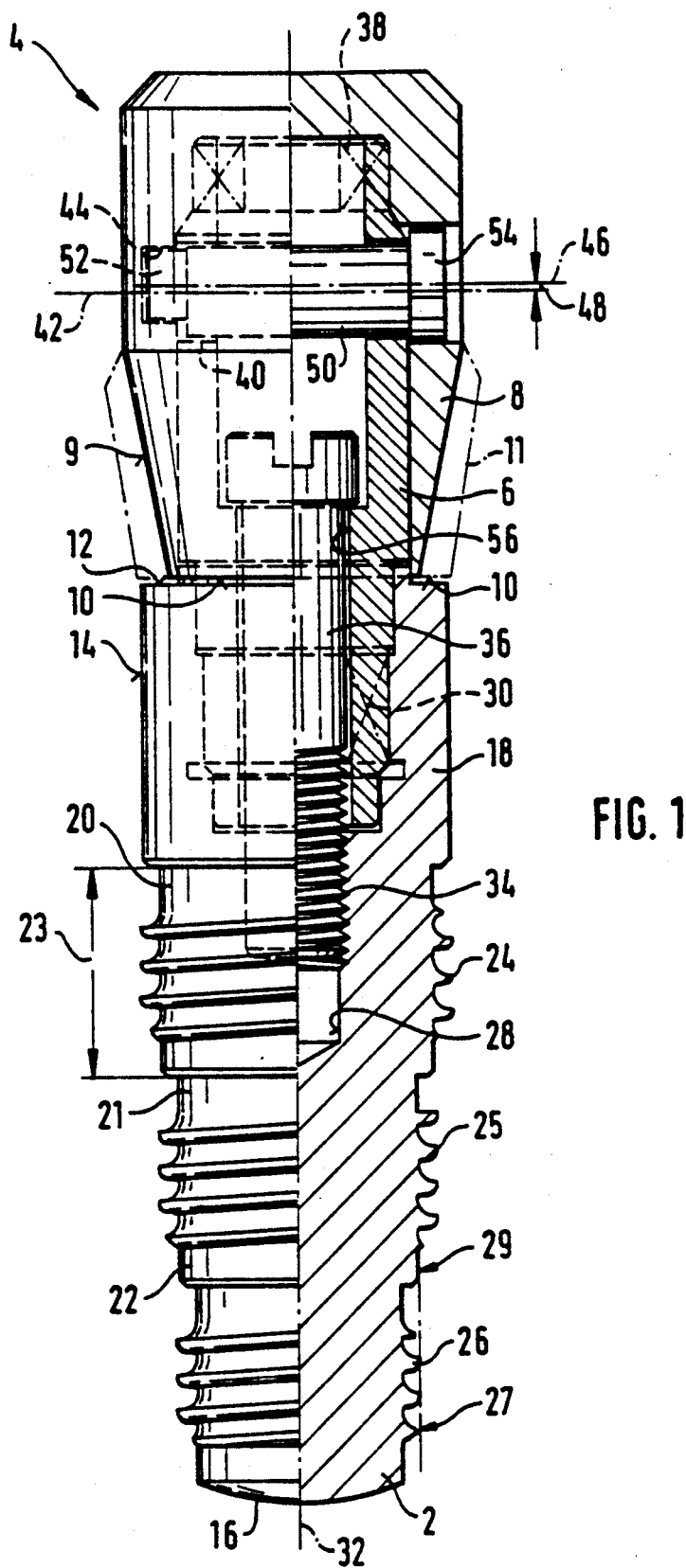
FIG. 1 is a side elevation of the dental implant of the invention partially in section along its axial plane.

FIG. 1 shows the dental implant partially in elevation and partially in an axial longitudinal section, with a post 2 which can be anchored in the jawbone, and a head 4 which can be joined to the post. The head 4 is constructed in two pieces, a coupling means 6 and a crown support 8. It is also within the scope of the invention, however, to construct the head 4 in one piece. The important thing in all configurations is that the bottom face 10, which in the illustrated embodiment is the bottom end of the crown support, is in close contact, preferably biased contact, against the bearing surface 12 of the post 2. Otherwise, the relationships and advantages described below in connection with the two-part configuration, as regards the formation of the bottom face 10 of the crown support 8, apply similarly to a one-piece head. The head 4, and in the case of the bipartite configuration shown here, its pot-shaped crown support 8 has an outer surface that tapers toward the post 2. Its bottom face 10 is thus smaller than it would be in the case of a cylindrical configuration with an outside diameter corresponding to that of the post 2. Due to this "diminution" of the bottom face 10, it is easier to work, and especially to grind or mill flat the ceramic coating applied to the face 10. Bottom face 10 and likewise at least a portion of the preferably conical outer surface 9 are provided with this ceramic oxide coating which may have a thickness ranging from a few micrometers to a few millimeters. The face 10 coated in this manner forms the one and only surface of the head 4 which must fit with the post 2, and it can be ground flat with very great precision.

The ceramic coating 11 on the outer surface 9 advantageously has a comparatively great thickness, as is indicated by the broken lines. The coating thickness is preferably established by making its outside diameter at its bottom face 10 substantially equal to the outside diameter of step 18 of post 2 at the bearing surface 12. Thus a desirably smooth transition is created from the head 4 to the post 2. In the case of such great thicknesses of the coating 11, it is possible within the scope of the invention for the end face of the crown support 8 to be set back a given distance from the bearing surface 12, because then the face 10 will be a part of the ceramic coating 11. Due to the comparatively great thickness of the coating 11, any applied force will be transmitted from the crown support 8 through the coating 11 and its bottom face to the bearing surface 12 of the post 2. The coating 11 is part of the head 4, and the bias is applied through the end face 10 regardless of the thickness of the coating.

The post 2 preferably is formed of metal, particularly of titanium or a titanium alloy, and the bearing surface 12 and/or the outer surface 14 are provided with a biologically compatible coating, especially of hydroxyapatite. The post 2 has a stepped profile in which the diameters of successive steps decrease toward the root end 16 of the post. The top step 18 adjacent the head 4 has a cylindrical outer surface, while the three other steps 20, 21, 22 have self-tapping threads 24, 25, 26 for turning and cutting into the jawbone. The three steps 20, 21, 22 provided with the threads are each of substantially the same length 23. It is especially important that the self-tapping thread 26 of step 22 adjacent the root end 16 has a crest diameter 27 that is no greater than the base diameter 29 of the next step 21 toward the head 4. The same applies to threads 25 and 24 with regard to the base diameter of step 20 and the outside diameter of step 18, respectively. As a general rule in accordance with the invention, the thread crest diameter of one step is equal to or smaller than the base diameter of the next-larger step. This assures that the dental implant can be inserted into a similarly stepped bore drilled in the jawbone such that afterward it needs to be screwed in only one step deeper. At the same time an optimum and full seating is assured throughout the length of all of the steps, which in the present example are three in number. It is to be understood that the bore must first be drilled into the jawbone so that the dental implant can be inserted sufficiently deeply into the prepared bore that it will need to be screwed in only one more step-length. It has furthermore been found to be especially desirable to provide the step 18 adjacent the head 4 with a substantially cylindrical outer surface 14 whose outside diameter is at least equal to the outside or thread crest diameter of step 20 which adjoins it toward the apical end 16.

The threads 24, 25, 26 of the three steps 20, 21, 22 are of different diameters but of the same thread pitch. The bases of the threads have a uniform diameter over the entire length of the step and the difficulties encountered with taper threading and/or tapered posts are avoided. Where a plurality of threaded steps are provided, the steps will each have substantially the same axial length. It is considered within the scope of the invention to provide only a single threaded step. For hygienic reasons in the implant area, at least the step which is adjacent the head 4, and has the greatest diameter, preferably has no thread. Basically, the post can thus have a first thread at the root end, which will be adjoined by the second step with a substantially smooth outside surface; each of these steps consequently will account for substantially half of the total length of the post. Embodiments having two threaded steps also lie within the scope of this invention. The illustrated embodiment, with three steps provided with threads, has been found to be especially desirable. In this embodiment, at least approximately three thread flights are provided on each of the threaded steps, so that only three turns are needed to screw it in. Since the post is simply inserted into the stepped bore in the jawbone leaving only the length of one step exposed, and then is screwed in for the length of only one step with three turns, the operating time is minimized without the fear of traumatizing the cortex with the screw thread.

A recess or cavity 28 provided in the interior of the post 2 comprises a portion 30 in the form of a hexagon with flat surfaces. This portion 30 serves to receive an inserted tool, such as an Imbus key, to enable a torque to be exerted about the longitudinal axis 32 in order to implant the post 2. Of course, portion 30 can also be configured to receive tools having other configurations in order to insert the post 2 into the jaw and screw it to a depth corresponding to the length of one step into the bore which has been drilled accordingly.

Toward the root end 16 the cavity 28 contains an internal thread 34 with a smaller diameter than that of portion 30. Internal thread 34 is spaced axially from portion 30. Thus damage to the internal thread 34 by a tool designed for portion 30 is reliably prevented.

Although the aforedescribed configuration with screw threads on the outer surfaces coaxial with the longitudinal axis has proven to be practical, it is also within the scope of the invention to use configurations which instead have gaps on the outside surfaces corresponding to U.S. Pat. No. 4,185,383. Unlike this previously known dental implant, however, the post of the present invention is not directly provided with a head where it emerges from the gum, but has a bearing surface for a separate head which contains the crown support. The stepped configuration of the post and the bearing surface it offers for the end face of the head that engages it under bias are important.

The coupling means 6 is fixedly joined to the post 2 by means of a screw 36, whose root end engages the internal thread 34 of the post. Immediately after the post is implanted, the cavity 28 is advantageously plugged with a temporary screw or the like (not shown). After the post has set in the jaw, any gum tissue that has overgrown the bearing surface 12 is cut open and the temporary screw is removed again so that the coupling means 6 can be introduced into the cavity 28 in the manner shown and fastened by means of the screw 36. To prevent any unacceptable torque from being exerted on the post when inserting the screw 36, the coupling means 6 has at least one planar outside surface 60 which contacts a lateral surface of portion 30 and forms an antirotational lock. The coupling means 6 has at its crown end a boss 38, preferably one having a hexagonal configuration. By means of an appropriate tool, such as a hexagonal wrench, the post 2 can be secured and held fast by the planar outer surface of the coupling means and portion 30 against unintentional rotation, so that, when screw 36 is screwed in, there is no danger of loosening the post 2.

The coupling means 6 furthermore contains a transverse bore 40 having a transverse axis 42 aligned at right angles to the longitudinal axis 32. As shown, the crown support 8 is pot-shaped with an opening facing toward the root end 16, and the coupling means 6 engages the inner cavity of the crown support 8. The crown support 8 contains a blind bore 44 which also is disposed at right angles to the longitudinal axis. The axis 46 of bore 44 is offset eccentrically from the transverse axis 42. In the illustrated position, the axis 46 is offset from the transverse axis 42 at a short distance 48 toward the crown end. In the transverse bore 40 there is an eccentric pin 50 which has an eccentrically disposed shaft 52 engaging the blind bore 44, and a likewise eccentrically disposed head 54 which lies in a through bore 56 coaxial with the blind bore 44.

By turning the pin, by means of the head 54 which contains a slot or the like for a screwdriver, the eccentric pin 50 is rotated, and the axis 46 shifts from the illustrated position toward the root end 16. This also causes the crown support 8 to shift toward the root end 16 such that the end face 10 of the crown support 8 is biased against the bearing surface 12 of the post 2. Consequently, there is no gap between the ceramic coated end face 10 and the bearing surface 12 of the post 2. Thus a bacteria-proof joint between the head 4 and the post 2 is assured in a very reliable manner. The eccentricity of the pin 52 and head 54, as well as the diameter of the associated bores 44, are established with great precision, and even the distance between the established. The same also applies to the axial distance between the transverse bore 40 and the transverse axis 42 from the bearing surface 12 of the post 2. Consequently, in accordance with the invention, by rotating the eccentric pin 50, a precise axial bias between the crown support 8 and the post 2 is established.

Figure 2:
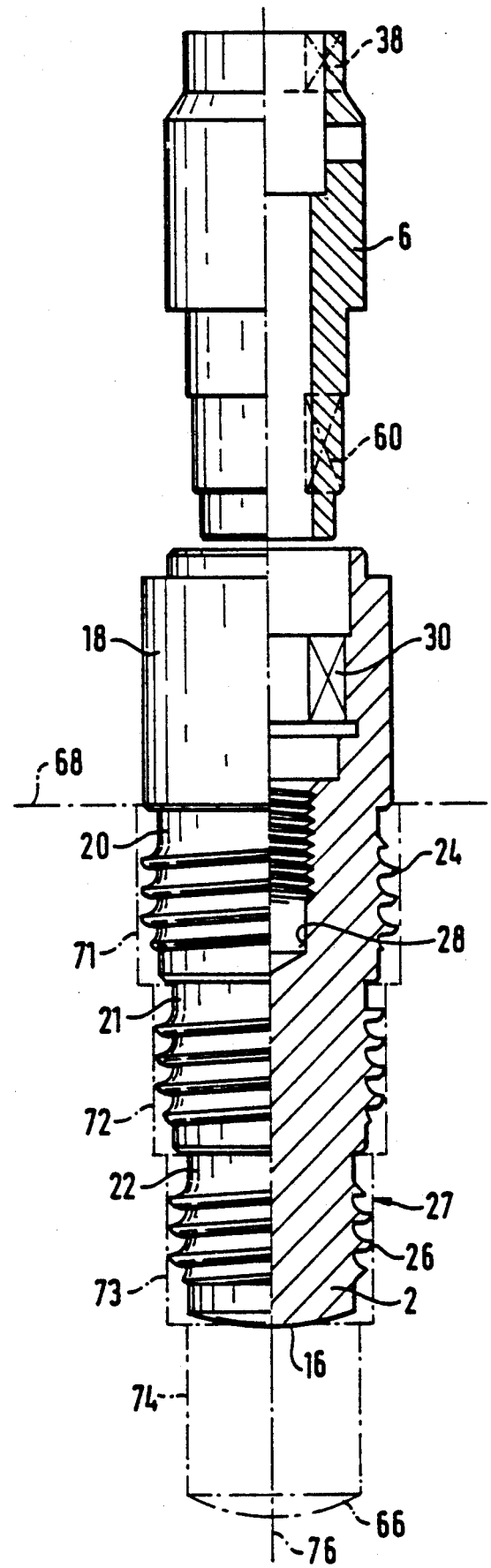
FIG. 2 is an exploded view of the post and coupling means of the implant of FIG. 1.

FIG. 2 is an exploded view of the coupling means 6 and post 2. Here, the planar outside surface 60 of the coupling means can be seen. If the coupling means 6 is inserted into the cavity 28, the cooperation of the outer surface 60 with the lateral surfaces of the hexagonal portion 30 assures that the coupling means 6 is locked against rotation with respect to the post 2.

The broken lines indicate the stepped bore 66 in the jawbone, whose upper edge 68 is likewise indicated by broken lines. The post 2 is shown in the position in which it has already been inserted into the jawbone with only one step-length remaining exposed. As can be seen, the bore 66 has four steps 71 to 74 whose respective diameters are each at least equal to the outside or crest diameter of the thread of the step of the post which is screwed into the next following step of the bore. The post is already inserted to ¾ of its total length into the stepped bore 66, so that a precise alignment with the longitudinal axis 76 of bore 66 is established. The post can then be screwed in by one more step-length, reliably and without special difficulty and without special measures for guiding the post.

Figure 3:
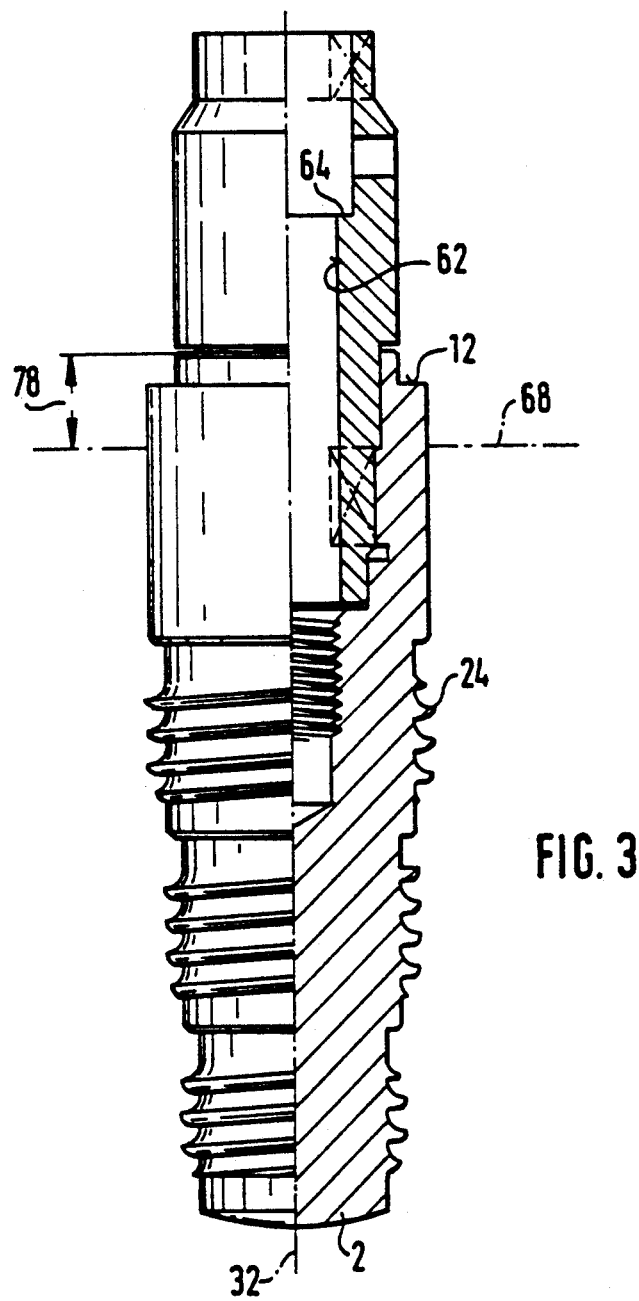
FIG. 3 is a view corresponding FIG. 2, but with the coupling means inserted.

In FIG. 3, the coupling means 6 is inserted into the blind hole 28 in the post 2. Here the longitudinal bore 62 for the screw for joining to the post 2 can easily be seen. This longitudinal bore 62 has an annular shoulder 64 for engagement by the head of the connecting screw which can be screwed with its external thread into the internal thread 34 of the post 2. The upper edge 68 of the jaw bone is indicated by the broken line. The step 18 and thus the upper end of the post 2 extends a distance 78 upwardly beyond the upper edge 68 of bore 66. The bearing surface 12 of the post 2 and the aforedescribed head consequently are situated in the gingival area.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A dental implant comprising a post anchorable in a jawbone of a dental patient and a replacement tooth head fastenable to said post, said post having a crown end provided with means for attaching said replacement tooth head and said post having an outer surface configured to form an apical root end opposite said crown end, said outer surface having at least two steps having substantially the same axial length with each step having a substantially constant base diameter along the length of the step, and with each step toward said apical root end having a respective base diameter which is smaller than the base diameter of the adjacent step toward said crown end, at least one of said steps carrying a screw thread; wherein each step which carries a thread has a thread crest diameter which is at most equal to the base diameter of the adjacent step situated toward said crown end, and wherein upon implantation said post can be freely inserted into a stepped bore in the jawbone down to all but one last step length and then can be screwed this last step length further into the jawbone.

2. A dental implant according to claim 1, wherein all of said steps which carry a screw thread are substantially equal in length.

3. A dental implant according to claim 1, wherein the step situated nearest said crown end has a substantially cylindrical outer surface with an outside diameter which is at least equal to the thread crest diameter of a thread-carrying adjacent step situated toward said apical root end.

4. A dental implant according to claim 1, wherein the step situated nearest said crown has a substantially cylindrical outer surface, and said crown end is provided with a recess in which said replacement tooth head is fastenable.

5. A dental implant according to claim 4, wherein said had comprises a pot-shaped crown support portion and fastening means for attaching said head to said post.

6. A dental implant according to claim 5, wherein said crown support has a locking surface which engages a mating surface in said recess to secure said crown support against rotation with respect to said post.

7. A dental implant according to claim 6, wherein said locking surface on said crown support is a flat outer surface on said crown support.

8. A dental implant according to claim 1, wherein said replacement tooth head has an end face which tightly engages a bearing face on said crown end of said post, and said head has an outer circumferential surface adjoining said end face which is partly surrounded by a gum of said dental patient when said dental implant is implanted in said patient.

9. A dental implant according to claim 8, wherein said end face of said replacement tooth head is provided with a smooth, flat ceramic coating.

10. A dental implant according to claim 9, wherein at least a portion of said outer circumferential surface of said head is likewise provided with a ceramic coating.

11. A dental implant according to claim 9, wherein said outside surface of said post adjacent said bearing surface of said crown end has a diameter substantially equal that of said ceramic coated end face of said replacement tooth head.

12. A dental implant according to claim 8, wherein said end face of said replacement tooth head is axially biased against said bearing face of said post.

13. A dental implant comprising a post anchorable in a jawbone of a dental patient and a replacement tooth head fastenable to said post, said post having a crown end provided with means for attaching said replacement tooth head and said post having an outer surface configured to form an apical root end opposite said crown end, said outer surface having at least two steps having substantially the same axial length with each step toward said apical root end having a respective base diameter which is smaller than the base diameter of the adjacent step toward said crown end, at least one of said steps carrying a screw thread; wherein each step which carries a thread has a thread crest diameter which is at most equal to the base diameter of the adjacent step situated toward said crown end; wherein upon implantation said post can be freely inserted into a stepped bore in the jawbone down to all but one last step length and then can be screwed this last step length further into the jawbone, and wherein the outside diameter of the threads of each thread carrying step other than the largest diameter thread carrying step is at most equal to the diameter of a jawbone bore into which the threads of the next larger diameter thread carrying step can be screwed; the steps of the stepped bore having substantially equal axial lengths, each step of said stepped bore having a substantially constant diameter along the length of the step, and each step of the stepped bore having a diameter which is at least as great as the base diameter of a corresponding step of said post outer surface and which is smaller than the thread crest diameter of said corresponding step of said post outer surface.

14. A dental implant comprising a post anchorable in a jawbone of a dental patient and a replacement tooth head fastenable to said post, said post having a crown end provided with means for attaching said replacement tooth head and said post having an outer surface configured to form an apical root end opposite said crown end, said outer surface having at least two steps with each step toward said apical root end having a respective base diameter which is smaller than the base diameter of the adjacent step toward said crown end, at least one of said steps carrying a screw thread; wherein each step which carries a thread has a thread crest diameter which is at most equal to the base diameter of the adjacent step situated toward said crown end, and upon implantation said post can be freely inserted into a stepped bore in the jawbone down to all but one last step length and then can be screwed this last step length further into the jawbone; the step situated nearest said crown having a substantially cylindrical outer surface; said crown end being provided with a recess in which said replacement tooth head is fastenable; said head comprising a pot-shaped crown support portion and fastening mans for attaching said head to said post; and said crown support being provided with a coupling means having a transverse bore and means for axially tightening said crown support axially against said post comprising an eccentric pin received in said transverse bore.

15. A dental implant according to claim 14, wherein said means for attaching comprise a recess in said crown end of said post having an internal thread in at least part of the interior thereof; said coupling means is provided with a longitudinal through-bore and an annular shoulder surrounding said through bore, and said coupling means is fastened to said post by extending a screw with an enlarged head through said through-bore and screwing said screw into said internal thread in said recess until the head of said screw engages said annular shoulder.

16. A dental implant comprising a post anchorable in a jawbone of a dental patient and a replacement tooth head fastenable to said post, said post having a crown end provided with means for attaching said replacement tooth head and said post having an outer surface configured to form an apical root end opposite said crown end, said outer surface having at least two steps with each step having a substantially constant base diameter along the length of the step, and with each step toward said apical root end having a respective base diameter which is smaller than the base diameter of the adjacent step toward said crown end, at least one of said steps carrying a screw thread; wherein each step which carries a thread has a thread crest diameter which is at most equal to the base diameter of the adjacent step situated toward said crown end, and upon implantation said post can be freely inserted into a stepped bore in the jawbone down to all but one last step length and then can be screwed this last step further into the jawbone, and said outer surface has four steps, the step nearest said crown end having a cylindrical outer surface, and the three steps nearest said apical root end carrying screw threads.

17. A dental implant comprising a post anchorable in a jawbone of a dental patient and a replacement tooth head fastenable to said post, said post having a crown end provided with means for attaching said replacement tooth head and said post having an outer surface configured to form an apical root end opposite said crown end, said outer surface having at least two threaded steps with each step having a substantially constant base diameter along the length of the step, and with each step toward said apical root end having a respective base diameter which is smaller than the base diameter of the adjacent step toward said crown end; wherein upon implantation said post can be freely inserted into a stepped bore in the jawbone down to all but one last step length and then can be screwed this last step length further into the jawbone.

18. A dental implant according to claim 17, wherein each step other than the largest diameter step situated toward the crown end is threaded and has a thread crest diameter which is at most equal to the base diameter of the adjacent step situated toward said crown end.

19. A dental implant according to claim 17, wherein each threaded step carries a substantially cylindrical thread.

20. A dental implant according to claim 17, wherein each threaded step has a thread base diameter which is substantially equal to the diameter of the corresponding step of the stepped bore in which it is screwed.

* * * * *